(12) United States Patent
Noji

(10) Patent No.: US 10,849,590 B2
(45) Date of Patent: Dec. 1, 2020

(54) DYNAMIC STATE IMAGING SYSTEM CONFIGURED TO ACQUIRE A PLURALITY OF IMAGES INDICATING A DYNAMIC STATE OF A SUBJECT AT PREDETERMINED TIME INTERVALS

(71) Applicant: Konica Minolta, Inc., Tokyo (JP)

(72) Inventor: Sho Noji, Kokubunji (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 16/193,472

(22) Filed: Nov. 16, 2018

(65) Prior Publication Data
US 2019/0150871 A1   May 23, 2019

(30) Foreign Application Priority Data

Nov. 20, 2017   (JP) .................................. 2017-222355

(51) Int. Cl.
*A61B 6/00*   (2006.01)

(52) U.S. Cl.
CPC .............. *A61B 6/541* (2013.01); *A61B 6/46* (2013.01); *A61B 6/486* (2013.01); *A61B 6/487* (2013.01); *A61B 6/52* (2013.01); *A61B 6/527* (2013.01); *A61B 6/5258* (2013.01); *A61B 6/5264* (2013.01); *A61B 6/54* (2013.01); *A61B 6/542* (2013.01); *A61B 6/545* (2013.01); *A61B 6/467* (2013.01); *A61B 6/503* (2013.01)

(58) Field of Classification Search
CPC ........... A61B 6/46; A61B 6/467; A61B 6/486; A61B 6/487; A61B 6/503; A61B 6/5258; A61B 6/5264; A61B 6/527; A61B 6/54; A61B 6/541; A61B 6/542; A61B 6/545; A61B 6/52; A61B 6/40; A61B 6/42; A61B 6/4208; A61B 6/4233; A61B 6/4283; A61B 6/44; A61B 6/4452
USPC .......................................... 378/8, 42, 62, 95
See application file for complete search history.

(56) References Cited

U.S. PATENT DOCUMENTS

| | | | | |
|---|---|---|---|---|
| 7,050,537 B2* | 5/2006 | Tsujii | ....................... | A61B 6/02 378/95 |
| 7,620,444 B2* | 11/2009 | Le | .......................... | A61B 5/113 600/428 |
| 7,826,888 B2* | 11/2010 | Sendai | ................... | G01N 23/04 378/8 |
| 7,839,975 B2* | 11/2010 | Nakamura | ............... | A61B 5/08 378/65 |
| 7,965,814 B2* | 6/2011 | Ma | ......................... | A61B 6/541 378/62 |

(Continued)

FOREIGN PATENT DOCUMENTS

| JP | 5125750 B2 | 1/2013 |
|---|---|---|
| JP | 5672147 B2 | 2/2015 |

*Primary Examiner* — Allen C. Ho
(74) *Attorney, Agent, or Firm* — Cantor Colburn LLP

(57) ABSTRACT

A dynamic state imaging system includes a hardware processor that acquires period information on a period of a subject's dynamic state having periodicity, and controls a radiation imaging apparatus to acquire dynamic state images of a plurality of periods by assigning a same phase as an imaging start timing for each period of the subject's dynamic state, based on the period information, and performing imaging at predetermined time intervals from the imaging start timing for each period.

8 Claims, 6 Drawing Sheets

(56) References Cited

U.S. PATENT DOCUMENTS

| | | | | |
|---|---|---|---|---|
| 8,014,489 B2* | 9/2011 | Oshima | A61B 6/50 | 378/8 |
| 8,131,050 B2* | 3/2012 | Tamai | A61B 6/4233 | 382/132 |
| 8,254,522 B2* | 8/2012 | Takagi | A61B 6/00 | 378/95 |
| 8,315,354 B2* | 11/2012 | Takeda | A61B 6/466 | 378/62 |
| 8,317,705 B2* | 11/2012 | Stapf | A61B 5/416 | 382/128 |
| 8,328,793 B2* | 12/2012 | Birkenbach | A61B 1/00039 | 606/1 |
| 8,358,740 B2* | 1/2013 | Nakatsugawa | A61B 6/102 | 378/116 |
| 8,363,786 B2* | 1/2013 | Nakatsugawa | A61B 6/4441 | 378/116 |
| 8,483,456 B2* | 7/2013 | Nagatsuka | A61B 5/08 | 382/128 |
| 8,488,738 B2* | 7/2013 | Morita | A61B 6/583 | 378/62 |
| 8,790,264 B2* | 7/2014 | Sandler | A61B 7/026 | 600/481 |
| 9,020,097 B2* | 4/2015 | Iwakiri | A61B 6/4283 | 378/42 |
| 9,044,194 B2* | 6/2015 | Noji | A61B 5/08 | |
| 9,064,302 B2* | 6/2015 | Muraoka | A61B 6/507 | |
| 9,177,389 B2* | 11/2015 | Sumitomo | G06T 7/285 | |
| 9,198,628 B2* | 12/2015 | Shimada | A61B 6/4291 | |
| 9,326,745 B2* | 5/2016 | Muraoka | A61B 6/4233 | |
| 9,492,135 B2* | 11/2016 | Yamato | A61B 6/503 | |
| 9,639,952 B2* | 5/2017 | Shimamura | A61B 6/4233 | |
| 9,665,935 B2* | 5/2017 | Yamato | A61B 6/50 | |
| 9,704,242 B2* | 7/2017 | Fujiwara | G06T 7/0016 | |
| 9,743,900 B2* | 8/2017 | Graw | A61B 6/541 | |
| 9,801,555 B2* | 10/2017 | Noji | A61B 5/113 | |
| 9,836,842 B2* | 12/2017 | Yamato | A61B 6/5288 | |
| 9,901,317 B2* | 2/2018 | Shimamura | A61B 6/463 | |
| 9,947,093 B2* | 4/2018 | Tsunomori | G06T 7/13 | |
| 9,972,088 B2* | 5/2018 | Fujiwara | G06T 7/0016 | |
| 9,990,735 B2* | 6/2018 | Toyama | A61B 6/486 | |
| 10,026,188 B2* | 7/2018 | Muraoka | G06T 5/008 | |
| 10,115,037 B2* | 10/2018 | Kasai | G06K 9/6215 | |
| 10,143,435 B2* | 12/2018 | Hosoki | A61B 6/486 | |
| 10,149,658 B2* | 12/2018 | Tsunomori | A61B 6/5217 | |
| 10,223,790 B2* | 3/2019 | Kasai | G06T 7/0016 | |
| 10,242,446 B2* | 3/2019 | Muraoka | G06T 5/005 | |
| 10,297,012 B2* | 5/2019 | Futamura | A61B 5/7285 | |
| 10,413,269 B2* | 9/2019 | Nagano | A61B 6/06 | |
| 10,540,767 B2* | 1/2020 | Matsutani | A61B 6/5288 | |
| 10,586,328 B2* | 3/2020 | Matsutani | G06T 11/00 | |
| 10,614,568 B2* | 4/2020 | Noji | A61B 6/507 | |
| 10,687,772 B2* | 6/2020 | Futamura | G06T 5/002 | |
| 10,702,192 B2* | 7/2020 | Nakazawa | A61B 5/1128 | |

* cited by examiner

DYNAMIC STATE IMAGING SYSTEM CONFIGURED TO ACQUIRE A PLURALITY OF IMAGES INDICATING A DYNAMIC STATE OF A SUBJECT AT PREDETERMINED TIME INTERVALS

CROSS-REFERENCE TO RELATED APPLICATION

The present application claims priority under 35 U.S.C § 119(e) to Japanese Patent Application No. 2017-222355, filed on Nov. 20, 2017, the entire contents of which are incorporated herein by reference.

BACKGROUND

Technological Field

The present invention relates to a dynamic state imaging system.

Description of the Related Art

For conventional still image imaging and diagnosis of a subject by radiation using a film/screen or stimulable phosphor plate, attempts are being made that images a dynamic state image of the subject by using a semiconductor image sensor such as a flat panel detector (FPD) and applies the dynamic state image for diagnosis. Specifically, utilizing quick responsiveness in reading and erasing image data of the semiconductor image sensor, pulsed radiation is continuously radiated from a radiation source in synchronization with reading and erasing timings of the semiconductor image sensor, and imaging is performed a plurality of times per second, whereby a dynamic state of a subject is imaged (for example, see JP 5672147 B2 and JP 5125750 B2).

However, in conventional dynamic state imaging, imaging is always performed at constant time intervals from an imaging start without being conscious of a period of a dynamic state of a subject. For that reason, as illustrated in FIG. 6, phases of frame images of respective periods acquired by the dynamic state imaging are not basically the same as each other, and it has been impossible to effectively utilize dynamic state images of a plurality of periods.

SUMMARY

An object of the present invention is to enable dynamic state images of a plurality of periods to be effectively utilized by acquiring dynamic state images having the same phases at each period of the plurality of periods.

To achieve the abovementioned object, according to an aspect of the present invention, a dynamic state imaging system reflecting one aspect of the present invention comprises a hardware processor that acquires period information on a period of a subject's dynamic state having periodicity, and controls a radiation imaging apparatus to acquire dynamic state images of a plurality of periods by assigning a same phase as an imaging start timing for each period of the subject's dynamic state, based on the period information, and performing imaging at predetermined time intervals from the imaging start timing for each period.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

[Configuration of Dynamic State Imaging System 100]

First, a configuration of the present embodiment will be described.

Figure 1:
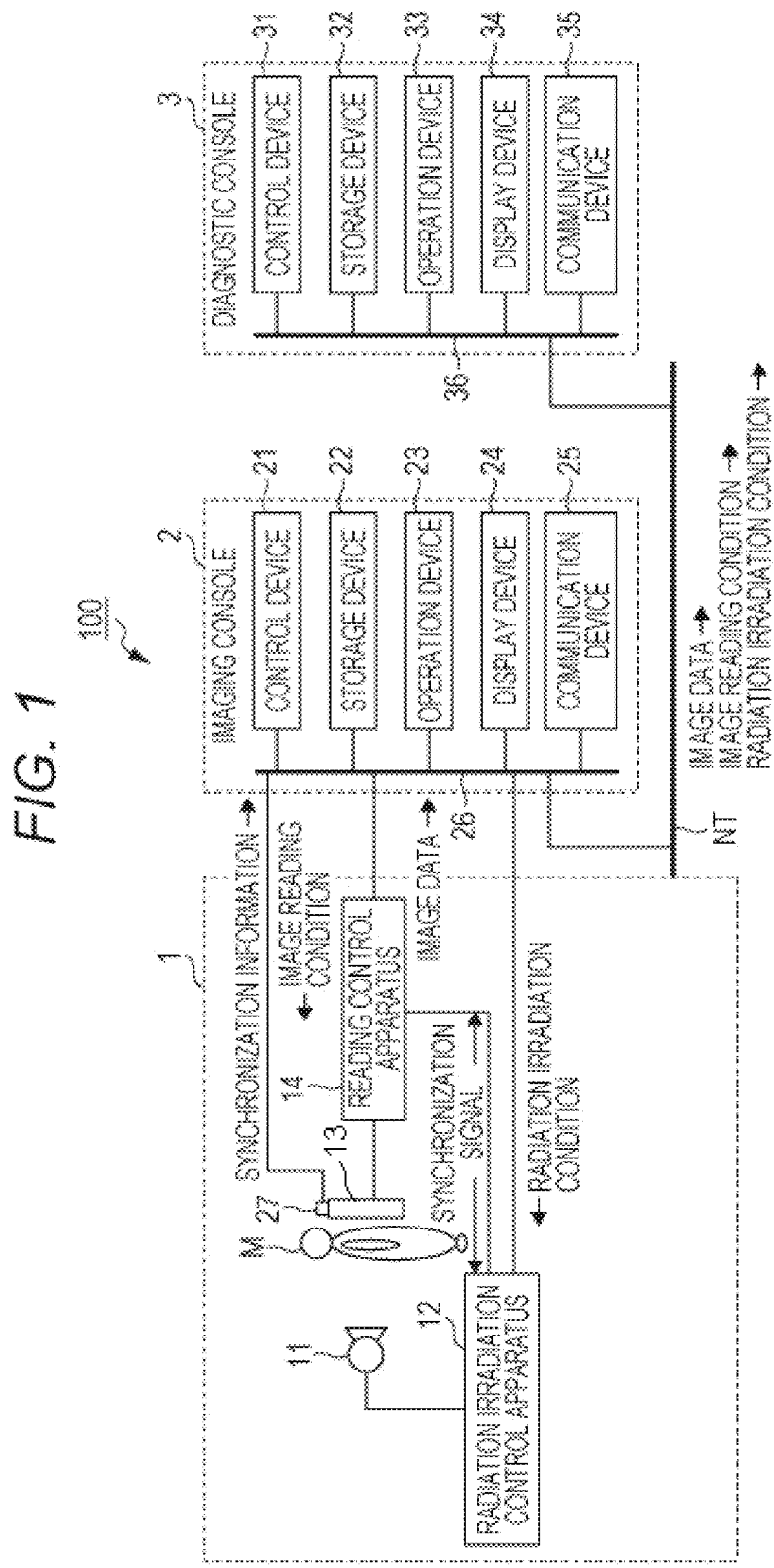
FIG. 1 is a diagram illustrating an overall configuration of a dynamic state imaging system according to an embodiment of the present invention.

FIG. 1 illustrates an overall configuration example of a dynamic state imaging system 100 in the present embodiment.

As illustrated in FIG. 1, the dynamic state imaging system 100 includes an imaging apparatus 1 and an imaging console 2 connected via a communication cable or the like, and a diagnostic console 3 connected to the imaging console 2 via a communication network NT such as a local area network (LAN). The apparatuses constituting the dynamic state imaging system 100 conform to the digital image and communications in medicine (DICOM) standard, and communication between the apparatuses is performed in accordance with DICOM.

[Configuration of Imaging Apparatus 1]

The imaging apparatus 1 is a radiation imaging apparatus that images a subject's dynamic state having periodicity, such as a form change of expansion and contraction of a lung accompanying respiratory movement, and a beat of a heart. Dynamic state imaging means to acquire a plurality of images indicating a dynamic state of a subject by repeatedly irradiating the subject with radiation such as a pulsed X-ray at predetermined time intervals (pulse irradiation) or continuously irradiating the subject with the radiation at a low dose rate (continuous irradiation), and reading a radiation image at predetermined time intervals. A series of images obtained by the dynamic state imaging is called a dynamic state image. In addition, each of the plurality of images constituting the dynamic state image is referred to as a frame image. In the following embodiment, an example will be described in which dynamic state imaging of a chest is performed by pulse irradiation.

A radiation source 11 is arranged at a position facing a radiation detecting device 13 across a subject M, and irradiates the subject M with radiation (X-ray) in accordance with control of a radiation irradiation control apparatus 12.

The radiation irradiation control apparatus 12 is connected to the imaging console 2, and performs radiation imaging by controlling the radiation source 11 on the basis of radiation irradiation conditions input from the imaging console 2. The radiation irradiation conditions input from the imaging console 2 include, for example, a pulse rate, a pulse width, a pulse interval, the number of imaging periods per dynamic state imaging, the number of imaging frames per period (the number of times of imaging), a value of an X-ray tube current, a value of an X-ray tube voltage, and an additional filter type. The pulse rate is the number of times of radiation irradiation per second, and coincides with a frame rate described later. The pulse width is a radiation irradiation time per radiation irradiation. The pulse interval is a time from a radiation irradiation start to the next radiation irradiation start, and coincides with a frame interval described later.

The radiation detecting device 13 includes a semiconductor image sensor such as a flat panel detector (FPD). The FPD includes a glass substrate, for example, and a plurality of detecting elements (pixels) is arranged in a matrix at a predetermined position on the substrate, the detecting elements each detecting radiation emitted from the radiation source 11 and transmitted through at least the subject M depending on its intensity, and converting the radiation detected into an electric signal to accumulate the signal. Each pixel includes a switching device such as a thin film transistor (TFT). Examples of the FPD include an indirect conversion type that converts an X-ray into an electric signal by a photoelectric conversion element via a scintillator, and a direct conversion type that directly converts an X-ray into an electric signal, and any of them may be used.

The radiation detecting device 13 is provided to face the radiation source 11 across the subject M.

A reading control apparatus 14 is connected to the imaging console 2. The reading control apparatus 14 controls the switching device of each pixel of the radiation detecting device 13 on the basis of image reading conditions input from the imaging console 2 to switch reading of the electric signal accumulated in each pixel, and reads the electric signal accumulated in the radiation detecting device 13 to acquire image data. The image data is a frame image. A pixel signal value of the frame image represents a density value. Then, the reading control apparatus 14 outputs the frame image acquired to the imaging console 2. The image reading conditions include, for example, a frame rate, a frame interval, a pixel size, and an image size (matrix size). The frame rate is the number of frame images to be acquired per second, and coincides with the pulse rate. The frame interval is a time from a frame image acquiring operation start to the next frame image acquiring operation start, and coincides with the pulse interval.

Here, the radiation irradiation control apparatus 12 and the reading control apparatus 14 are connected to each other, and mutually exchange synchronization signals to synchronize radiation irradiation operation with image reading operation.

[Configuration of Imaging Console 2]

The imaging console 2 outputs the radiation irradiation conditions and the image reading conditions to the imaging apparatus 1 and controls the radiation imaging and reading operation of the radiation image by the imaging apparatus 1, and displays the dynamic state image acquired by the imaging apparatus 1 for confirmation whether or not the image is suitable for diagnosis or confirmation of positioning by an imaging technician or an imaging practitioner.

As illustrated in FIG. 1, the imaging console 2 includes a control device 21, a storage device 22, an operation device 23, a display device 24, and a communication device 25, and the devices are connected to each other by a bus 26.

The control device 21 includes a central processing unit (CPU) and random access memory (RAM). The CPU of the control device 21 reads a system program and various processing programs stored in the storage device 22 depending on operation of the operation device 23 to deploy the programs in the RAM, and executes various types of processing such as imaging control processing described later in accordance with the programs deployed, to centrally control operation of each device of the imaging console 2 and the radiation irradiation operation and reading operation of the imaging apparatus 1. The control device 21 functions as a period information acquiring device and a control device.

The storage device 22 includes a nonvolatile semiconductor memory or a hard disk. The storage device 22 stores data such as various programs executed by the control device 21, parameters necessary for execution of processing by the programs, or processing result. For example, the storage device 22 stores a program for executing the imaging control processing illustrated in FIG. 2. In addition, the storage device 22 stores predetermined conditions among the radiation irradiation conditions and the image reading conditions. The various programs are each stored in a form of a readable program code, and the control device 21 sequentially executes operation according to the program code.

The operation device 23 includes a keyboard including a cursor key, a numeral input key, and various function keys, and a pointing device such as a mouse, and outputs an instruction signal input by key operation on a keyboard or mouse operation, to a control device 21. In addition, the operation device 23 may include a touch panel on a display screen of the display device 24, and in this case, outputs an instruction signal input via the touch panel to the control device 21.

The display device 24 includes a monitor such as a liquid crystal display (LCD) or a cathode ray tube (CRT), and displays an input instruction, data, and the like from the operation device 23 in accordance with an instruction of a display signal input from the control device 21.

The communication device 25 includes a LAN adapter, a modem, and a terminal adapter (TA), and controls data transmission/reception with each apparatus connected to the communication network NT.

A dynamic state detecting device 27 detects information indicating a dynamic state of the subject M and outputs a temporal change in the information (dynamic state detection information) to the control device 21. When the subject M is a lung field, the lung field moves with the respiratory movement, so that, for example, a respiration measuring instrument such as a respiration sensor, a spirometer, or a respiration monitor belt, and a sound collecting apparatus such as a microphone that collects a sound (for example, a breath sound) generated by an examinee, can be used as the dynamic state detecting device 27. The sound generated by the examinee may be a voice emitted by the examinee while breathing. A period in which a voice comes out can be regarded as exhalation (contraction phase of the lung field), and a period in which no voice comes out can be regarded as inhalation (expansion phase of the lung field). When the subject M is a heart, for example, a heart rate measuring instrument such as an electrocardiograph can be used as the dynamic state detecting device 27. Note that, the dynamic state detecting device 27 is preferably attached at a position that does not overlap the lung field during dynamic state imaging. For example, in the case of an electrocardiograph, the electrocardiograph is preferably attached to an arm or the like.

[Configuration of Diagnostic Console 3]

The diagnostic console 3 is a dynamic state image processing apparatus that acquires a dynamic state image from the imaging console 2 and applies image processing to the dynamic state image acquired and displays the image processed.

As illustrated in FIG. 1, the diagnostic console 3 includes a control device 31, a storage device 32, an operation device 33, a display device 34, and a communication device 35, and the devices are connected to each other by a bus 36.

The control device 31 includes a CPU and RAM. The CPU of the control device 31 reads a system program and various processing programs stored in the storage device 32 depending on operation of the operation device 33 to deploy the programs in the RAM, and centrally controls operation of each device of the diagnostic console 3 in accordance with the programs deployed. The control device 31 functions as an extracting device, a dynamic state image creating device, and a comparing device.

The storage device 32 includes a nonvolatile semiconductor memory or a hard disk. The storage device 32 stores data such as various programs executed by the control device 31, parameters necessary for execution of processing by the programs, or processing results. The various programs are each stored in a form of readable program code, and the control device 31 sequentially executes operation according to the program code.

The storage device 32 stores the dynamic state image imaged in the past in association with an identification ID, patient information (examinee information. For example, a patient ID, and the name, height, weight, age, and gender of the patient (examinee)), examination information (for example, an examination ID, an examination date, and a subject part (subject M; lung or heart)), and the like.

The operation device 33 includes a keyboard including a cursor key, a numeral input key, and various function keys, and a pointing device such as a mouse, and outputs an instruction signal input by key operation on a keyboard or mouse operation by a user, to a control device 31. In addition, the operation device 33 may include a touch panel on a display screen of the display device 34, and in this case, outputs an instruction signal input via the touch panel to the control device 31.

The display device 34 includes a monitor such as an LCD or a CRT, and performs various displays in accordance with an instruction of a display signal input from the control device 31.

The communication device 35 includes a LAN adapter, a modem, and a TA, and controls data transmission/reception with each apparatus connected to the communication network NT.

[Operation of Dynamic State Imaging System 100]

Next, operation will be described of the dynamic state imaging system 100 in the present embodiment.

(Operation of Imaging Apparatus 1 and Imaging Console 2)

First, imaging operation by the imaging apparatus 1 and the imaging console 2 will be described.

The imaging practitioner first operates the operation device 23 of the imaging console 2 to input the patient information and the examination information of the examinee. Next, positioning is performed by arranging the subject part (subject M) between the radiation source 11 and the radiation detecting device 13. In addition, instruction about a respiratory state (for example, normal respiration) is given to the examinee. When imaging preparation is completed, a radiation irradiation instruction is input by operation of the operation device 23.

When the radiation irradiation instruction is input by the operation device 23, the imaging control processing is executed in the imaging console 2. Hereinafter, the imaging control processing will be described.

Figure 2:
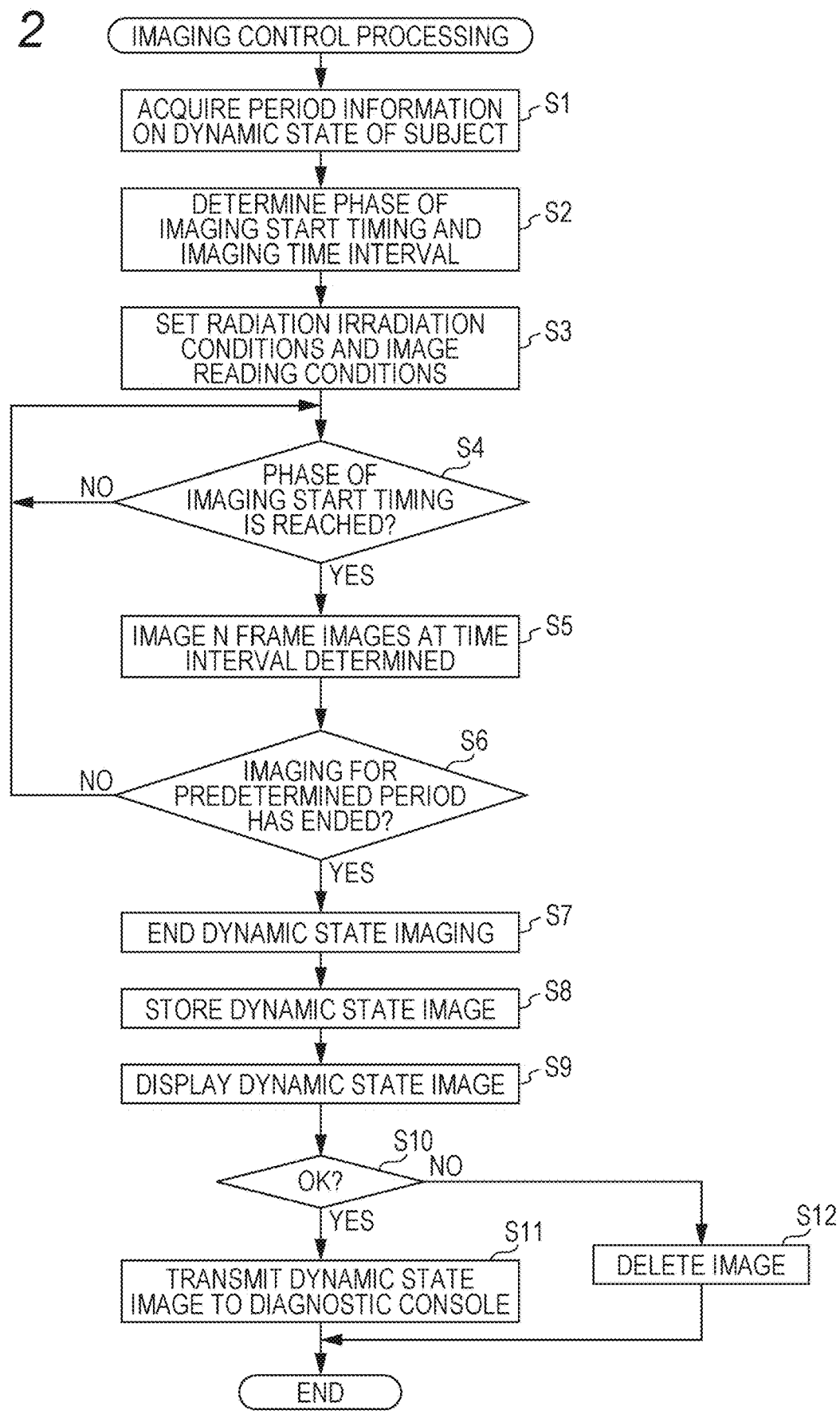
FIG. 2 is a flowchart illustrating imaging control processing executed by a control device of an imaging console of FIG. 1.

FIG. 2 illustrates imaging control processing executed by the control device 21 of the imaging console 2. The imaging control processing is executed by cooperation between the control device 21 and the programs stored in the storage device 22.

First, the control device 21 acquires period information on the dynamic state of the subject M on the basis of the dynamic state detection information output from the dynamic state detecting device 27 (step S1).

For example, on the basis of information (waveform) indicating the temporal change in the dynamic state detection information of the subject M output from the dynamic state detecting device 27, for example, a timing of a predetermined feature point of the dynamic state (for example, a transition point from inhalation to exhalation, a midpoint between exhalation and inhalation, or a transition point from exhalation to inhalation, when the subject M is a lung field) is set as a base point of one dynamic state period, and a time from the timing to when the feature point is detected next is acquired as a time taken for one period (in other words, a period).

Next, the control device 21 assigns the same phase of each period to an imaging start timing, and determines an imaging time interval of the frame images (pulse interval, frame interval) by dividing the period by the number of imaging frames (number of times of imaging) N per period (step S2), and sets the radiation irradiation conditions and image reading conditions including the imaging time interval of the frame images determined, in the radiation irradiation control apparatus 12 and the reading control apparatus 14 (step S3). The radiation irradiation conditions and the image reading conditions include the number of imaging frames N per dynamic state period, the number of imaging periods, the imaging time interval of the frame images, and the phase of the dynamic state assigned to the imaging start timing (for example, a maximum exhalation position, and a maximum inhalation position, when the subject M is a lung field).

Next, on the basis of the dynamic state detection information and the period information output from the dynamic state detecting device 27, the control device 21 waits until the dynamic state of the subject M reaches the phase of the imaging start timing (step S4).

When it is determined that the dynamic state of the subject M has reached the phase of the imaging start timing (step S4; YES), the control device 21 controls the radiation irradiation control apparatus 12 and the reading control apparatus 14 of the imaging apparatus 1 to image N frame images at the time interval determined in step S2 (step S5).

In the imaging apparatus 1, N times of radiation irradiation is performed by the radiation source 11 at the pulse interval set in the radiation irradiation control apparatus 12, and image data (frame images) are acquired by the radiation detecting device 13. The frame images acquired are transmitted to the imaging console 2, and sequentially stored in the storage device 22.

Next, the control device 21 determines whether or not imaging for a predetermined period (for a plurality of periods) has ended (step S6). When it is determined that the imaging for the predetermined period has not ended (step S6; NO), the control device 21 returns to step S4.

When it is determined that the imaging for the predetermined period has ended (step S6; YES), the control device 21 outputs an instruction of ending the dynamic state imaging to the radiation irradiation control apparatus 12 and the reading control apparatus 14, to end the dynamic state imaging (step S7).

The frame images acquired by the imaging are sequentially input to the imaging console 2, and the control device 21 stores the frame images input, in the storage device 22 in association with the respective numbers (frame numbers) each indicating imaging order (step S8), and causes the display device 24 to display the frame images (step S9). The imaging practitioner confirms positioning and the like with the dynamic state image displayed, and determines whether an image suitable for diagnosis is acquired by the imaging (imaging OK) or re-imaging is necessary (imaging NG). Then, a determination result is input by operation of the operation device 23.

When a determination result indicating the imaging OK is input by predetermined operation of the operation device 23 (step S10; YES), to each of a series of frame images acquired by the dynamic state imaging, information is added (for example, written in the header region of the image data in the DICOM format) such as the identification ID for identifying the dynamic state image, the patient information, the examination information, the radiation irradiation conditions, the image reading conditions, and the number (frame number) indicating the imaging order, and transmitted to the diagnostic console 3 via the communication device 25 (step S11). Then, the processing ends. On the other hand, when a determination result indicating the imaging NG is input by the predetermined operation of the operation device 23 (step S10; NO), the series of frame images stored in the storage device 22 are deleted (step S12), and the processing ends. In this case, re-imaging is necessary.

Figure 3:
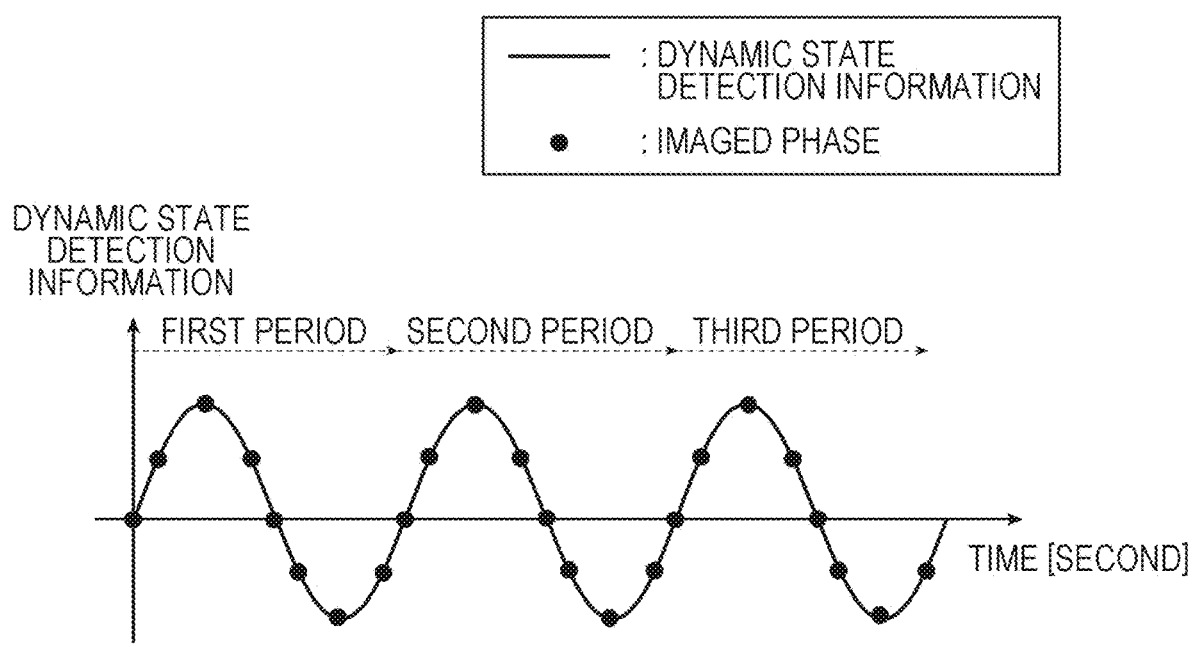
FIG. 3 is a diagram illustrating a temporal change in dynamic state detection information of a subject and imaging timings of frame images in the present embodiment.

FIG. 3 is a graph illustrating the temporal change in the dynamic state detection information of the subject M and timings at which the frame images are imaged. As illustrated in FIG. 3, in the imaging control processing, imaging is performed at timings at the same phase for each period of the dynamic state of the subject M. For example, for each period, imaging is performed at predetermined time intervals from a predetermined phase. Therefore, the dynamic state images can be acquired having the same phases at each period of the plurality of periods.

(Operation of Diagnostic Console 3)

Next, operation in the diagnostic console 3 will be described.

Figure 4:
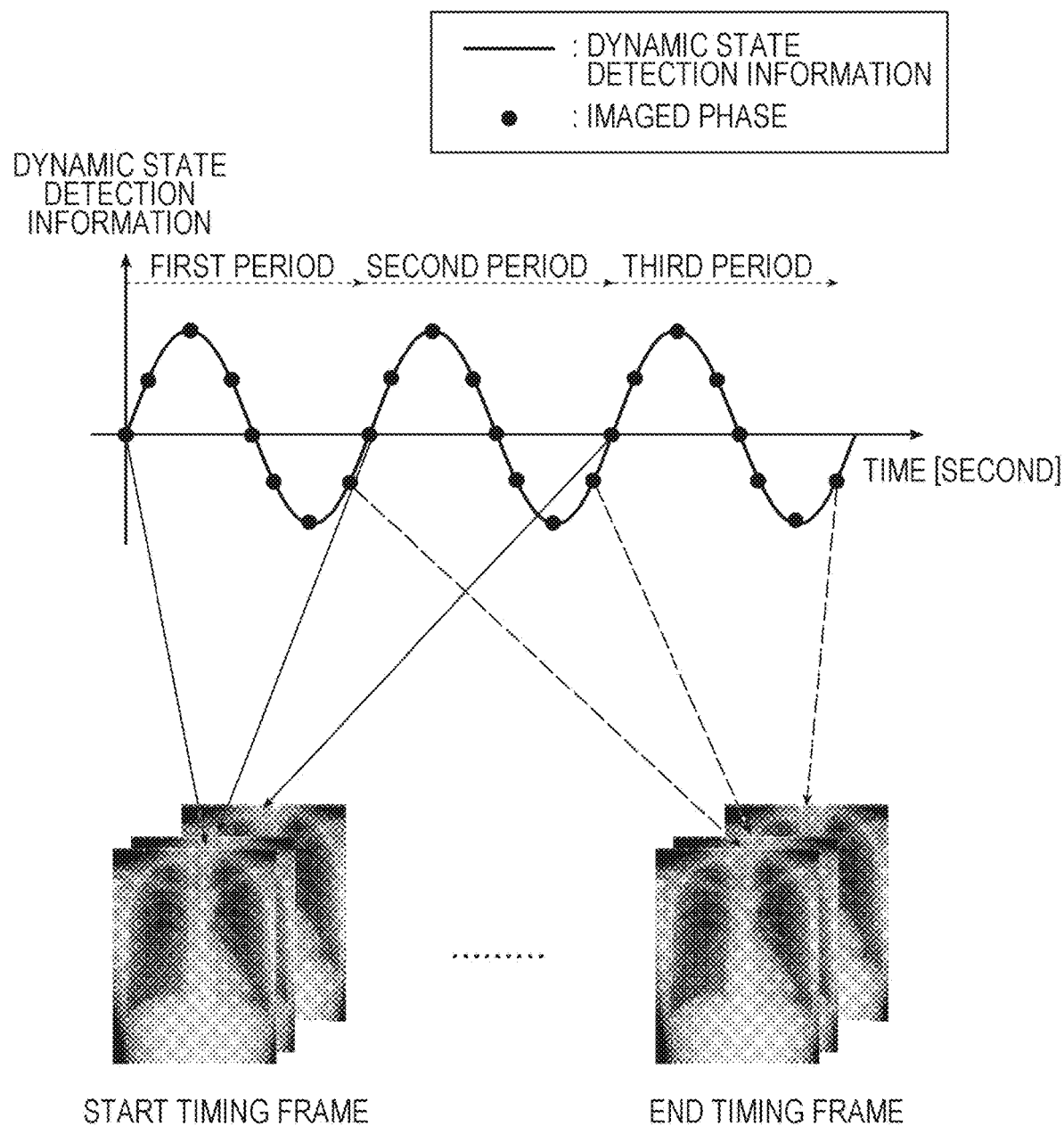
FIG. 4 is a diagram for explaining frame images at the same phase of a plurality of periods.

When a series of frame images of dynamic state images obtained by imaging the dynamic state of the subject M for a plurality of periods is received from the imaging console 2 via the communication device 35, the control device 31 of the diagnostic console 3 performs processing of at least one of the following (1) to (3) for each frame image at the same phase of the plurality of periods, as illustrated in FIG. 4.

(1) Aggregate Frame Images of the Plurality of Periods in One Period

A representative value (average value, added value, maximum value, minimum value, or median value) is calculated of pixel values (density values) of corresponding pixels (pixels at the same position) of the frame images at the same phase, and a dynamic state image for one period is created.

For the dynamic state image, a plurality of times of radiation irradiation is performed for imaging a plurality of frame images. For that reason, each frame image is imaged at a low dose to suppress exposure of the examinee, which results in an image with a lot of noise. Therefore, as described above, the density values of each pixel of frame images at the same phase of the plurality of periods are aggregated to make a dynamic state image for one period, whereby a dynamic state image can be acquired with reduced noise.

Above work is repeatedly performed and the dynamic state image for one period is created a plurality of times, whereby dynamic state images can also be acquired of the plurality of periods with reduced noise.

(2) Compare the Density Values of a Subject Region Between the Frame Images at the Same Phase A subject region (subject M's region) is extracted from each frame image, and a representative value (average value, added value, maximum value, minimum value, or median value) of the density value is calculated for the entire subject region, or for each small region obtained by dividing the subject region into a plurality of small regions, and representative values calculated are compared between the frame images at the same phase of the plurality of periods. Alternatively, the density values of each pixel are compared between the frame images at the same phase of the plurality of periods.

Here, if there is an abnormality in the subject M, states of the subject M do not coincide with each other even at the same phase in the dynamic state period. For example, there is a case in which a difference in the density value of the subject M becomes large between the frame images at the same phase. If there is no abnormality, the states of the subject M substantially coincide with each other at the same phase, and the difference in the density value is small between the frame images at the same phase. Therefore, as a method of comparing the density values, for example, a difference value is calculated for each region (for each pixel) of the frame images to be compared, and a group of the frame images of the phase in which the difference value is greater than or equal to a predetermined threshold (the difference becomes large) is displayed side-by-side. Alternatively, an image in which each region (each pixel) of the frame image is colored depending on the difference value may be displayed on the display device 34 (for example, red for greater than or equal to a predetermined threshold, and blue for less than the threshold).

As a result, it becomes possible to provide a doctor with a basis for determination to determine normality/abnormality of the subject M.

(3) Compare Shapes of the Subject Region Between the Frame Images at the Same Phase An index value representing a shape of the subject M is calculated such as the area of the subject region of each frame image, the length (for example, the distance between the apex of a lung and the diaphragm (the width of a heart)), the curvature of the contour, or the concordance rate of the contour shape, and index values calculated are compared between the frame images at the same phase of the plurality of periods.

As described above, if there is an abnormality in the subject M, states of the subject M do not coincide with each other even at the same phase in the dynamic state period. For example, there is a case in which a difference in shape becomes large. If there is no abnormality, the states of the subject M substantially coincide with each other at the same phase, and the difference in shape is small. Therefore, as a method of comparing the shapes, for example, a difference value is calculated of the index values of the frame images to be compared, and a group of the frame images of the phase in which the difference value is greater than or equal to a predetermined threshold (the difference becomes large) is displayed side-by-side.

As a result, it becomes possible to provide a doctor with a basis for determination to determine normality/abnormality of the subject M.

As described above, according to the dynamic state imaging system 100, the control device 21 of the imaging console 2 acquires the period information on the period of the subject M's dynamic state having the periodicity, and controls the imaging apparatus 1 to acquire the dynamic state image of the plurality of periods by assigning the same phase as the imaging start timing for each period of the subject M's dynamic state on the basis of the period information acquired, and performing imaging at predetermined time intervals from the imaging start timing for each period.

Therefore, the dynamic state images can be acquired having the same phases at each period of the plurality of periods, and the dynamic state images of the plurality of periods can be effectively utilized.

For example, the control device 21 calculates the time interval of the dynamic state imaging by dividing the time of one period of the dynamic state of the subject M by the predetermined number of times of imaging per period, whereby imaging of each period can be performed at the same phase.

In addition, the control device 31 of the diagnostic console 3 creates the dynamic state image in which the average values, added values, maximum values, minimum values, or median values of the density values of each pixel of the frame images at the same phase in the dynamic state images of the plurality of periods acquired by the imaging apparatus 1 are calculated and aggregated in one period. Therefore, the dynamic state image can be acquired with reduced noise.

The control device 31 of the diagnostic console 3 extracts the subject M's region from respective frame images of the dynamic state images of the plurality of periods acquired by the imaging apparatus 1, and compares the subject M's regions extracted from the frame images at the same phase of the dynamic state images of the plurality of periods. For example, the control device 31 compares the average values, added values, maximum values, minimum values, or median values of the density values of individual pixels in the subject M's regions in the frame images at the same phase of the plurality of periods, or of the density values in individual small regions obtained by dividing the subject M's regions. Alternatively, the control device 31 compares the shapes of the subject M's regions in the frame images at the same phase of the plurality of periods. Therefore, it becomes possible to provide a doctor with information to be a basis for determination to determine normality/abnormality of the dynamic state of the subject M.

Note that, the description of the embodiment is a preferable example of the present invention, and this is not a limitation.

Figure 5:
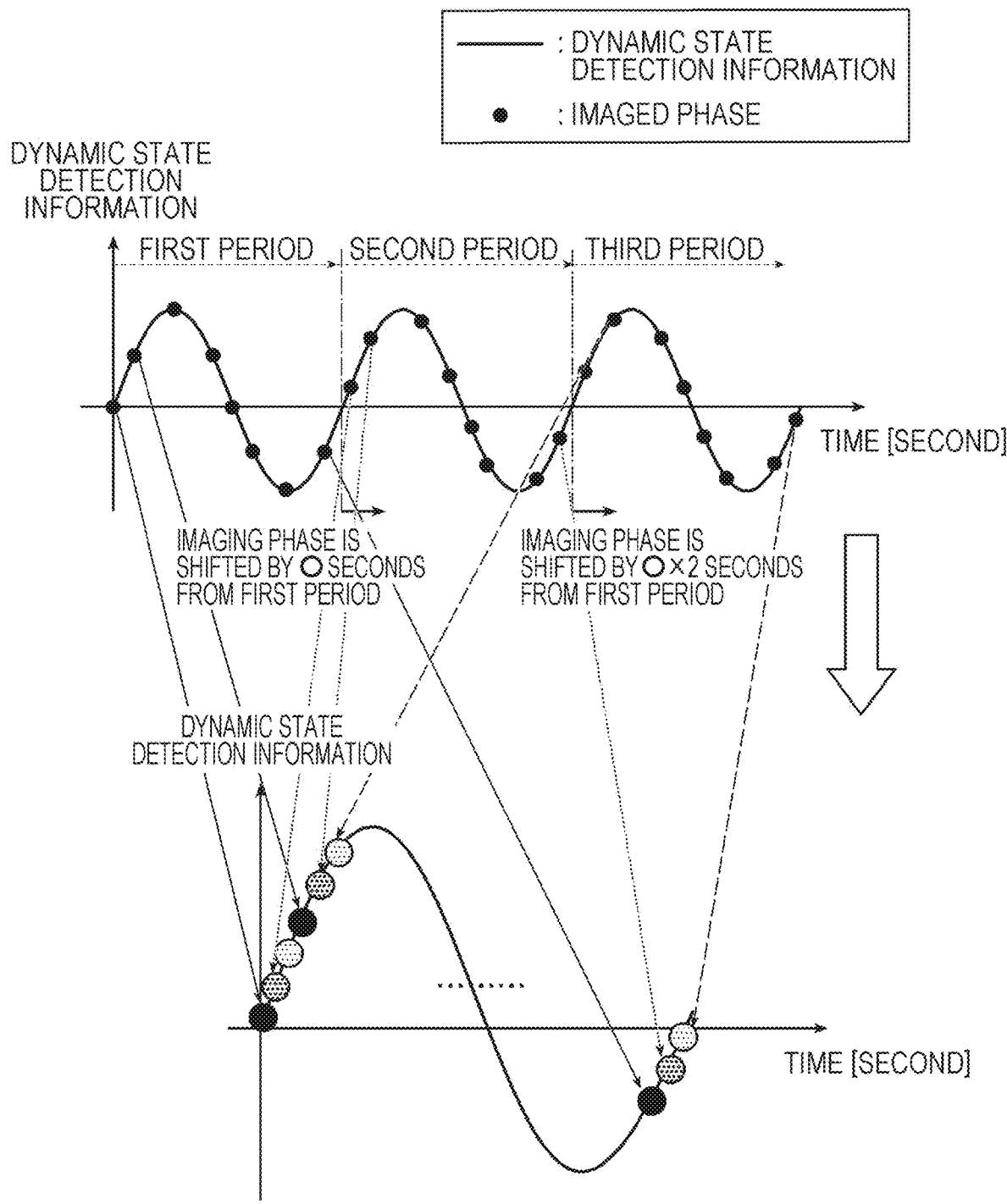
FIG. 5 is a diagram schematically illustrating a modification in which imaging phases are shifted by a predetermined interval for each period, and frame images are rearranged in accordance with the phases.
Figure 6:
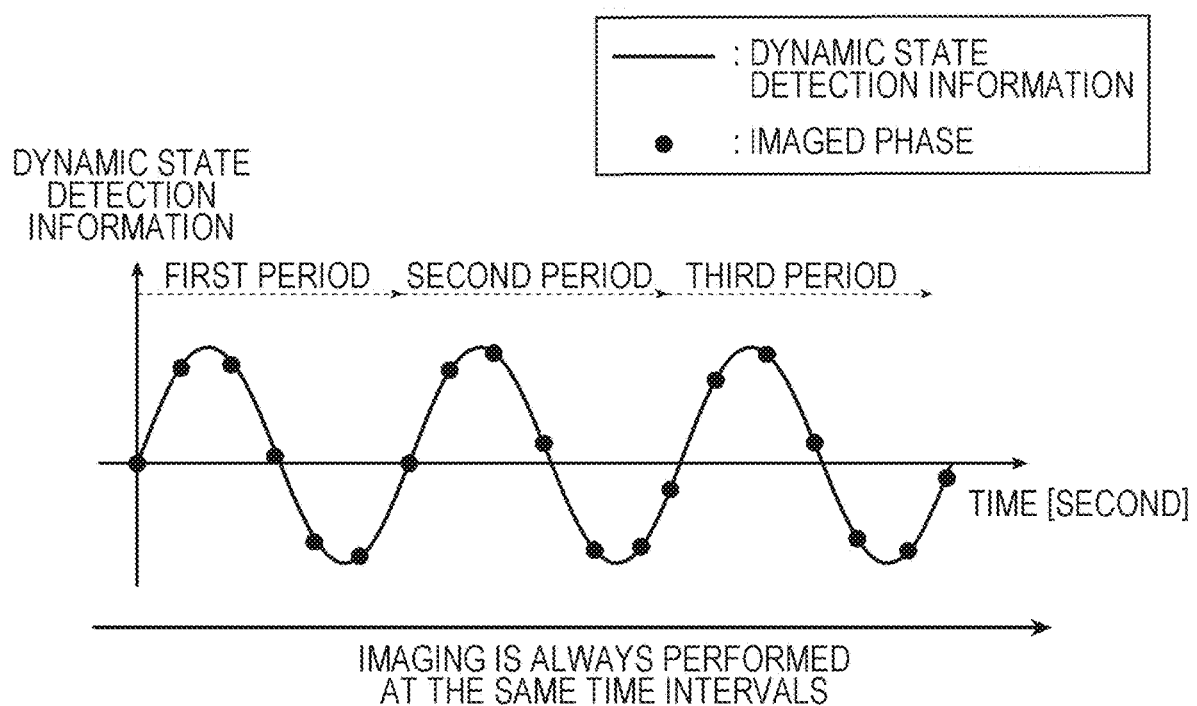
FIG. 6 is a diagram illustrating a temporal change in dynamic state detection information of a subject and imaging timings of frame images in a conventional technique.

For example, in the embodiment, the description has been made assuming that the control device 21 of the imaging console 2 controls the imaging apparatus 1 to image the frame images at the same phase in the plurality of periods; however, as illustrated in FIG. 5, the imaging apparatus 1 may be controlled to image the frame images by shifting the imaging phases by a predetermined interval for each period. For example, when the subject M is a heart, the frame images are imaged at 15 fps from the end diastole in the first period, the frame images are imaged at 15 fps from 0.02 second after the end diastole in the second period, the frame images are imaged at 15 fps from 0.04 second after the end diastole in the third period, and so on. Then, the frame images of the dynamic state images imaged by shifting the imaging timing are rearranged on the basis of the phases. As a result, it is possible to virtually acquire a dynamic state image with a high frame rate. Note that, the number of imaging periods is determined so that the imaging time interval between the frame images becomes constant when the frame images are rearranged.

In the embodiment, an example has been described in which the period information acquiring device that acquires the period information on the dynamic state of the subject M and the control device that controls the imaging apparatus 1 are included in the imaging console 2 separate from the imaging apparatus 1; however, the devices may be included in the imaging apparatus 1. In addition, the description has been made assuming that the dynamic state image creating device, the extracting device, and the comparing device are included in the diagnostic console 3; however, the devices may be included in the imaging apparatus 1 integrated with the imaging console 2, or in the imaging console 2. In other words, the dynamic state imaging system of the present invention may include a single apparatus, or may include a plurality of apparatuses.

In the embodiment, an example has been described in which the subject M is a lung field or a heart; however, the subject M may be, for example, a joint of limbs, and is not limited to the embodiment.

In the embodiment, an example has been described in which the control device 21 acquires the period information on the basis of the information indicating the temporal change in the dynamic state of the subject M acquired from the respiration measuring instrument, the heart rate measuring instrument, or the sound collecting apparatus that collects the sound generated by the examinee; however, when imaging is performed while causing the examinee to breath on the basis of a breathing instruction such as "inhale, exhale, . . . ", since the lung of the examinee moves in accordance with the breathing instruction, the information of the breathing instruction is acquired from a breathing instruction generating apparatus, as information indicating the temporal change in the dynamic state of the subject M, and the period information may be acquired on the basis of the information of the breathing instruction.

In the above descriptions, an example has been disclosed in which the hard disk or semiconductor nonvolatile memory is used as a computer readable medium for programs according to the present invention, but the medium is not limited to this example. As another computer readable medium, a portable recording medium such as CD-ROM can be applied. In addition, as a medium for providing data of the programs according to the present invention via a communication line, a carrier wave is also applied.

Besides, the detailed configuration of each apparatus constituting the dynamic state imaging system and detailed operation of each apparatus can be appropriately changed without departing from the spirit of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A dynamic state imaging system comprising:
   a hardware processor that acquires period information on a period of a subject's dynamic state having periodicity, and controls a radiation imaging apparatus to acquire dynamic state images of a plurality of periods by assigning a same phase as an imaging start timing for each period of the subject's dynamic state, based on the period information, and performing imaging at predetermined time intervals from the imaging start timing for each period;

wherein the hardware processor creates a dynamic state image, in which average values, added values, maximum values, minimum values, or median values of density values of an individual pixel of frame images at the same phase in the dynamic state images of the plurality of periods acquired by the radiation imaging apparatus are calculated and aggregated in one period.

2. The dynamic state imaging system according to claim 1, wherein the subject is a lung or a heart.

3. The dynamic state imaging system according to claim 2, wherein the hardware processor acquires the period information, based on information indicating a temporal change in the subject's dynamic state acquired from a respiration measuring instrument, a heart rate measuring instrument, a sound collecting apparatus that collects a sound generated by an examinee, or a breathing instruction generating apparatus.

4. The dynamic state imaging system according to claim 1, wherein the hardware processor calculates the predetermined time intervals, based on a time of one period of the period information acquired by the hardware processor and a predetermined number of times of imaging per period.

5. A dynamic state imaging system comprising:
a hardware processor that acquires period information on a period of a subject's dynamic state having periodicity, and controls a radiation imaging apparatus to acquire dynamic state images of a plurality of periods by assigning a same phase as an imaging start timing for each period of the subject's dynamic state, based on the period information, and performing imaging at predetermined time intervals from the imaging start timing for each period;

wherein the hardware processor extracts subject's regions from respective frame images of the dynamic state images of the plurality of periods acquired by the radiation imaging apparatus, and compares the subject's regions extracted from the frame images at the same phase of the dynamic state images of the plurality of periods.

6. The dynamic state imaging system according to claim 5, wherein the hardware processor compares average values, added values, maximum values, minimum values, or median values of density values of individual pixels in the subject's regions in the frame images at the same phase of the plurality of periods, or of density values in individual small regions obtained by dividing the subject's regions.

7. The dynamic state imaging system according to claim 5, wherein the hardware processor compares shapes of the subject's regions in the frame images at the same phase of the plurality of periods.

8. The dynamic state imaging system according to claim 5, wherein the hardware processor calculates the predetermined time intervals, based on a time of one period of the period information acquired by the hardware processor and a predetermined number of times of imaging per period.

\* \* \* \* \*